(12) United States Patent
Park et al.

(10) Patent No.: US 7,098,008 B2
(45) Date of Patent: Aug. 29, 2006

(54) SELECTED PRIMERS FOR DETECTION OF MAGE OR GAGE GENES FOR DIAGNOSIS OF CANCER AND METHODS OF USE

(75) Inventors: Jong Wook Park, Daegu (KR); Chang-Ho Jeon, Daegu (KR)

(73) Assignee: iC&G DO. Ltd., Taegu (KR)

( * ) Notice: Subject to any disclaimer, the term of this patent is extended or adjusted under 35 U.S.C. 154(b) by 428 days.

(21) Appl. No.: 10/286,380

(22) Filed: Nov. 1, 2002

(65) Prior Publication Data

US 2003/0104452 A1 Jun. 5, 2003

Related U.S. Application Data

(63) Continuation-in-part of application No. 10/258,828, filed as application No. PCT/KR01/00681 on Apr. 24, 2001.

(30) Foreign Application Priority Data

Apr. 25, 2000 (KR) .............................. 2000-21837

(51) Int. Cl.
*C12P 19/34* (2006.01)

(52) U.S. Cl. .......................... 435/91.2; 435/6

(58) Field of Classification Search ..................... None
See application file for complete search history.

(56) References Cited

U.S. PATENT DOCUMENTS

| 5,462,871 A | 10/1995 | Boon-Falleur et al. |
| 6,013,481 A | 1/2000 | DeBacker et al. |
| 6,057,105 A | 5/2000 | Hoon et al. |

FOREIGN PATENT DOCUMENTS

| WO | 98/46788 | * 10/1998 |

OTHER PUBLICATIONS

Kariko (BioTechniques, (Jun. 1995) 18(6)1048-9).*
De Plaen et al. (Immunogenetics (1994) 40:360-369).*
Park et al. (Journal of Immunological Methods, vol. 266, pp. 79-86, Aug. 2002).*
Maria Valeria Corrias et al., Expression of MAGE-1, MAGE-3 and MART-1 Genes in Neuroblastoma, Int. J. Cancer (Pred. Oncol) 69, 403-407 (1996).
T. Fujie et al., Expression of MAGE and BAGE genes in Japanese breast cancers, Annals Oncology 8: 369-372, 1997.
Hiroshi Inoue et al., Human Esophageal Carcinomas Frequently Express the Tumor-Rejection Antigens of *MAGE* Genes, Int. J. Cancer: 63, 523-526 (1995).
Hiroshi Inoue et al., The Expression of Tumor-Rejection Anigen "*MAGE*" Genes in Human Gastric Carcinomas, Gastroenterology 1995;109:1522-1525.
Jian Lu, et al., Expression of the MAGE Gene Family in Human Gastric Carcinoma, Anticancer Research 17: 3559-3563 (1997).
Masaki Mori, M.D. et al., Expression of MAGE Genes in Human Colorectal Carcinoma, Annals of Surgery, vol. 224, No. 2 183-188 (1996).
Vincenzo Russo et al., MAGE, BAGE and GAGE genes expression in fresh epithelial ovarian carcinomas (Letter to the Editor) Int. J. Cancer, 67, 457-460 (1996).
Vincenzo Russo et al., Expression of the *MAGE* Gene Family in Primary and Metastatic Human Breast Cancer: Implications for Tumor Antigen-Specific Immunotherapy, Int. J. Cancer (Pred. Oncol.) 64, 216-221 (1995).
Shigeki Shichijo et al., Expression of the MAGE gene family in human lymphocytic leukemia, Cancer immunol Immunother (1995) 41: 95-103.
Benoit Van den Eynde et al.; A New Family of Genes Coding for an Antigen Recognized by Autologous Cytolytic T Lymphocytes on a Human Melanoma, J. Exp. Med. , The Rockefeller University Press, vol. 182, Sep. 1995 689-698.
P. Weynants et al., Expression of MAGE Genes by Non-Small-Cell Lung Carcinomas, Int. J. Cancer 56, 826-829 (1994).
Nobuyuki Yamashita et al., High Frequency of the *MAGE-1* Gene Expression in Hepatocellular Carcinoma, Hepatology vol. 24, No. 6, 1437-1440, 1996.

\* cited by examiner

*Primary Examiner*—Juliet C. Switzer
(74) *Attorney, Agent, or Firm*—Orrick, Herrington & Sutcliffe LLP

(57) ABSTRACT

The present invention relates to primers for diagnosis of one or more kinds of cancers and a diagnosis kit comprising said primers. The primers are made from highly homologous areas of twelve MAGE subtypes and eight GAGE subtypes. The diagnostic kit comprising the said primers can detect six MAGE subtypes and eight GAGE subtypes respectively. The invention also includes methods for using the primers to diagnose the onset of cancer, to monitor the progression of disease, and to correlate the gene expression to the prognosis of disease.

8 Claims, 6 Drawing Sheets

[FIG. 1]
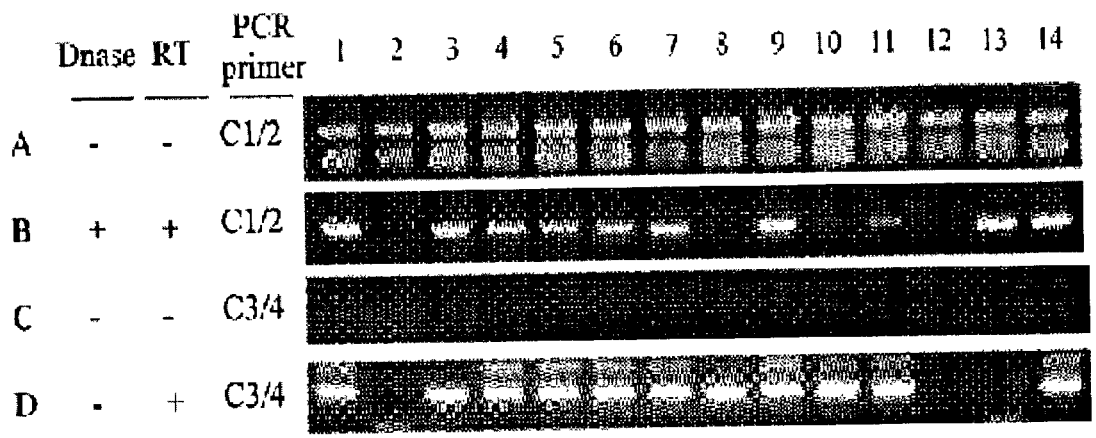
[FIG. 2]
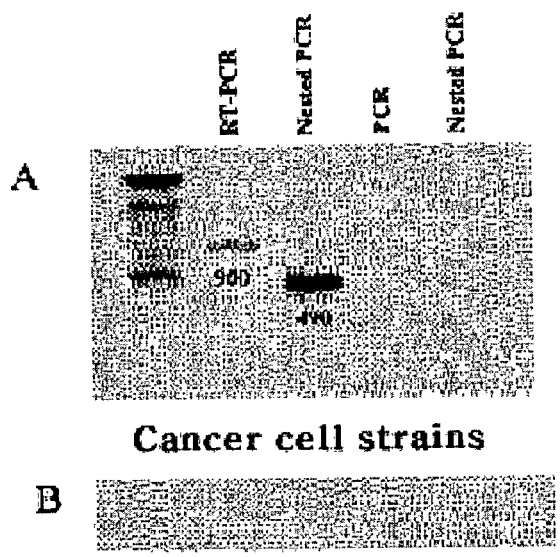
Cancer cell strains

[FIG. 3]

Cancer cell strains

| | 1 | 2 | 3 | 4 | 5 | 6 | 7 | 8 | 9 | 10 | 11 | 12 | 13 | 14 | Detection rate(%) |
|---|---|---|---|---|---|---|---|---|---|---|---|---|---|---|---|
| MAGE 1 | | | | | | | | | | | | | | | 50 |
| MAGE 2 | | | | | | | | | | | | | | | 35.7 |
| MAGE 3 | | | | | | | | | | | | | | | 57.1 |
| MAGE 4 | | | | | | | | | | | | | | | 35.7 |
| MAGE 5 | | | | | | | | | | | | | | | 7.1 |
| MAGE 6 | | | | | | | | | | | | | | | 14.2 |
| MAGE 1-6 | | | | | | | | | | | | | | | 78.6 |

[FIG. 4]

| | 1 | 2 | 3 | 4 | 5 | 6 | 7 | 8 | 9 | 10 | 11 | 12 | Detection rate(%) |
|---|---|---|---|---|---|---|---|---|---|---|---|---|---|
| MAGE-1 | | | | | | | | | | | | | 66.7 |
| MAGE-2 | | | | | | | | | | | | | 41.7 |
| MAGE-3 | | | | | | | | | | | | | 66.7 |
| MAGE-4 | | | | | | | | | | | | | 58.3 |
| MAGE-5 | | | | | | | | | | | | | 25.0 |
| MAGE-6 | | | | | | | | | | | | | 33.3 |
| MAGE 1-6 | | | | | | | | | | | | | 91.2 |

[FIG. 5]
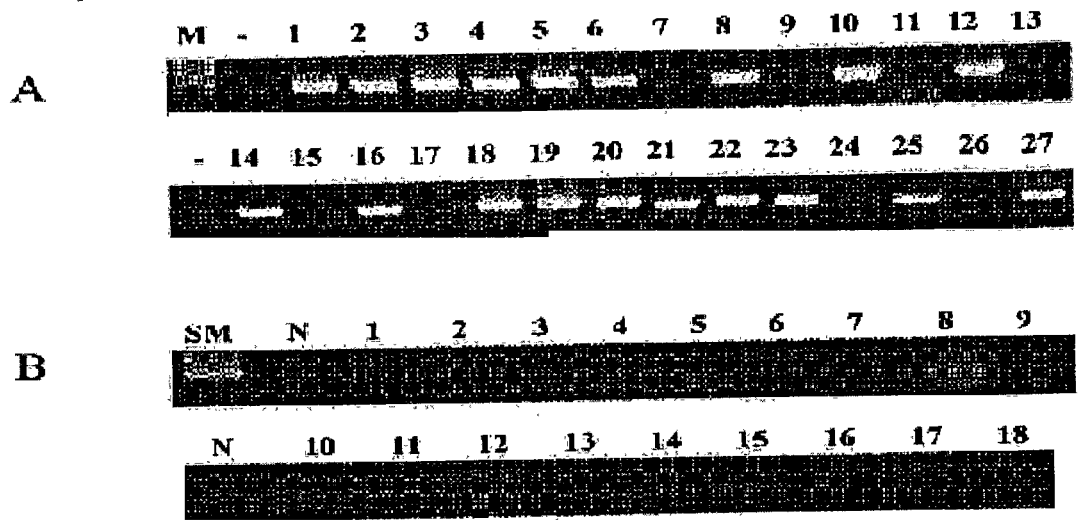
[FIG. 6]
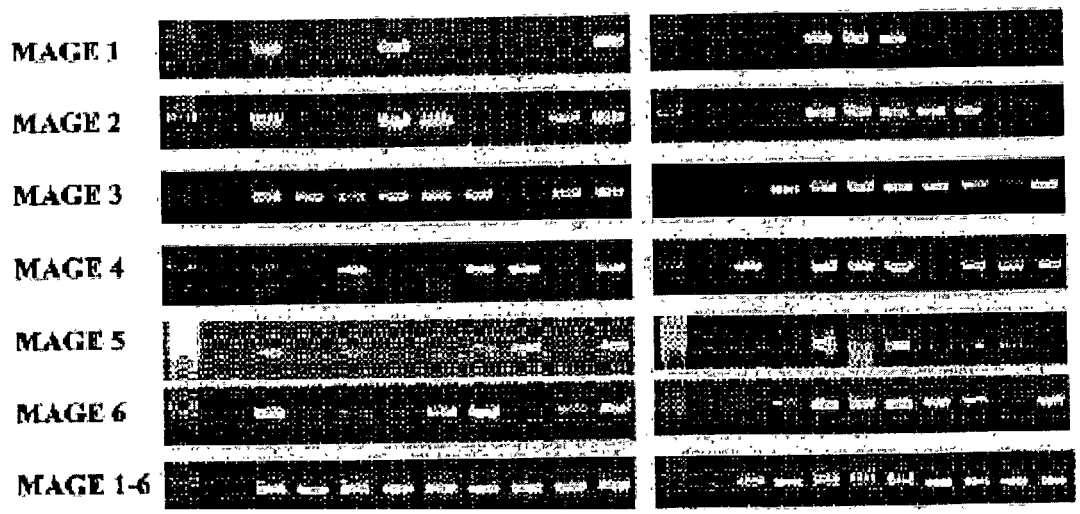

[FIG. 7]
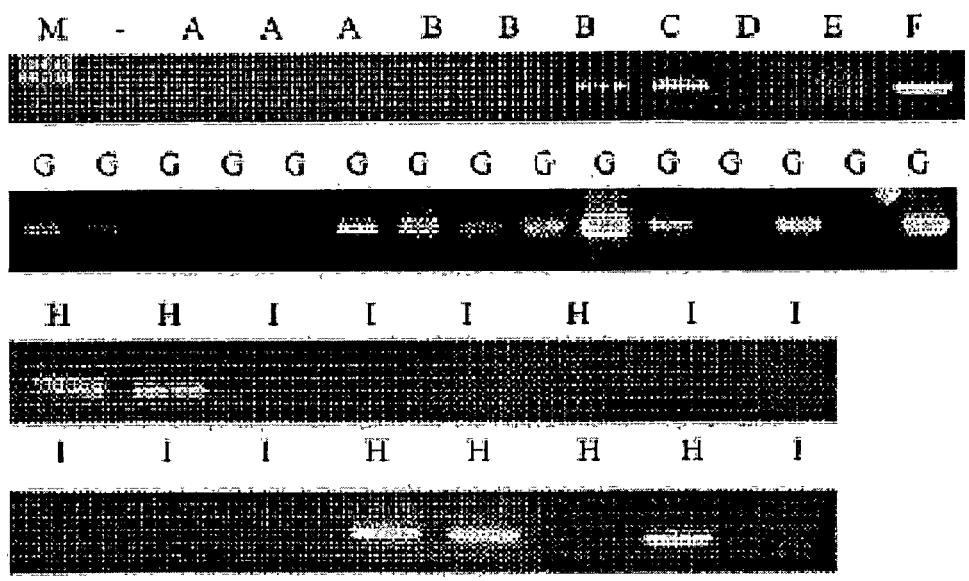
[FIG. 8]
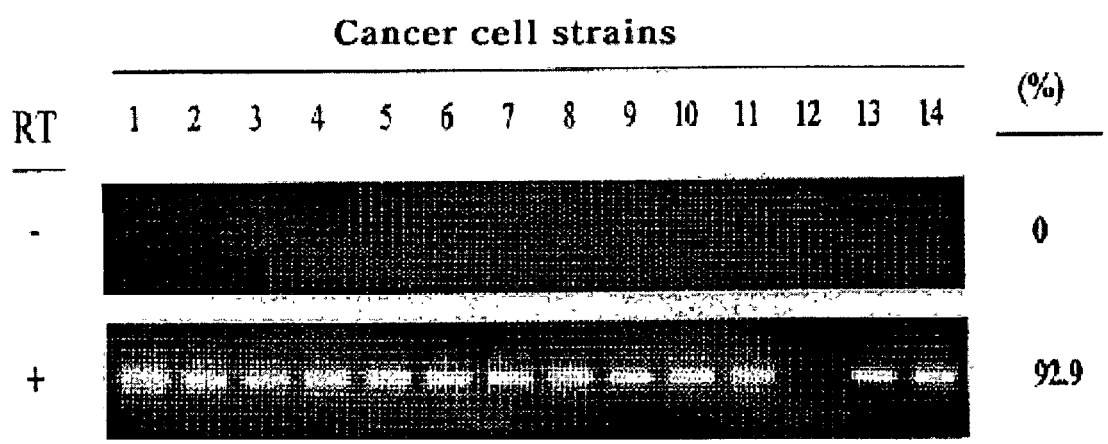

[FIG. 9]
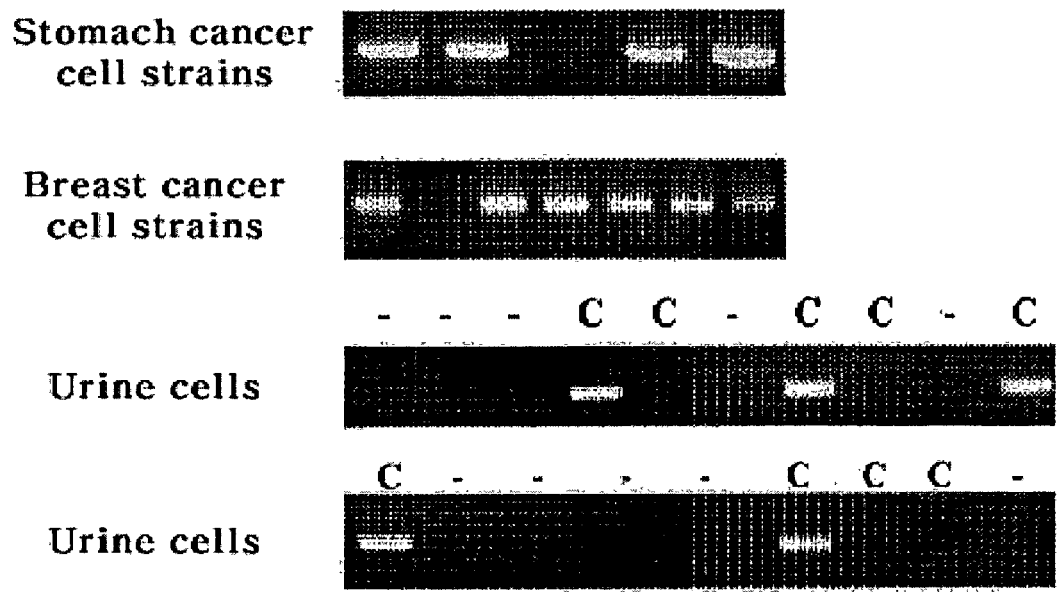
[FIG. 10]
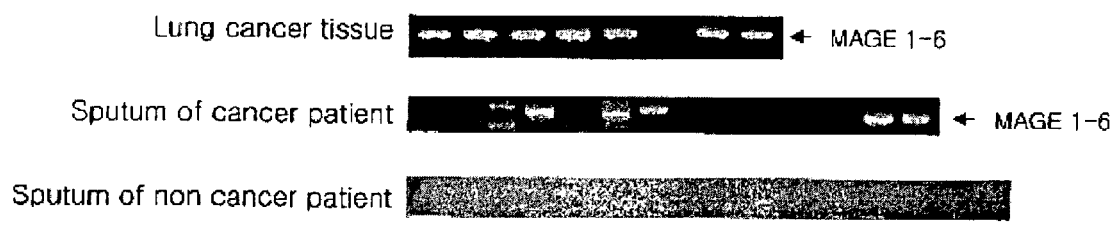

[FIG. 11]
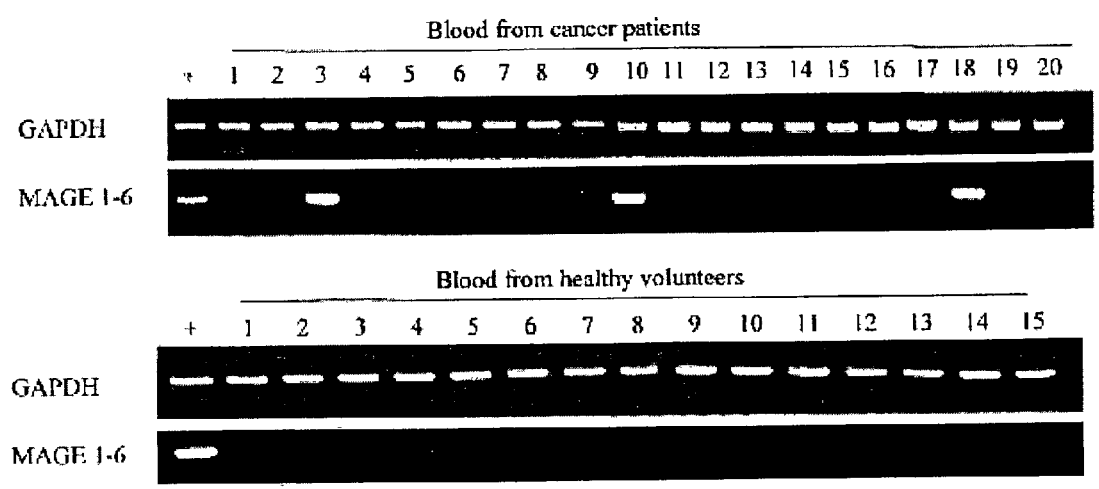

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Primer targeting MAGE 1-6; sense primer type

<400> SEQUENCE: 1
ggtcacaaag gcagaaatgc t                                            21

<210> SEQ ID NO 2
<211> LENGTH: 23
<212> TYPE: DNA
<213> ORGANISM: Artificial sequence
<220> FEATURE:
<223> OTHER INFORMATION: Primer targeting MAGE 1-6; antisense primer
      type

<400> SEQUENCE: 2
gcccttggac cccacaggaa ctc                                            23

<210> SEQ ID NO 3
<211> LENGTH: 19
<212> TYPE: DNA
<213> ORGANISM: Artificial sequence
<220> FEATURE:
<223> OTHER INFORMATION: Primer targeting MAGE 1-6; sense primer type

<400> SEQUENCE: 3
ctgaaggaga agatctgcc                                                 19

<210> SEQ ID NO 4
<211> LENGTH: 21
<212> TYPE: DNA
<213> ORGANISM: Artificial sequence
<220> FEATURE:
<223> OTHER INFORMATION: Primer targeting MAGE 1-6; antisense primer
      type

<400> SEQUENCE: 4
ctccaggtag ttttcctgca c                                              21

<210> SEQ ID NO 5
<211> LENGTH: 23
<212> TYPE: DNA
<213> ORGANISM: Artificial sequence
<220> FEATURE:
<223> OTHER INFORMATION: Primer targeting MAGE 1-6; sense primer type
<220> FEATURE:
<221> NAME/KEY: misc_feature
<222> LOCATION: (20)..(20)
<223> OTHER INFORMATION: w = a or t

<400> SEQUENCE: 5
ctgaaggaga agatctgccw gtg                                            23

<210> SEQ ID NO 6
<211> LENGTH: 22
<212> TYPE: DNA
<213> ORGANISM: Artificial sequence
<220> FEATURE:
<223> OTHER INFORMATION: Primer targeting MAGE 1-6; antisense primer
      type

<400> SEQUENCE: 6
ccagacattt ctgcctttgt ga                                             22

<210> SEQ ID NO 7
<211> LENGTH: 20
<212> TYPE: DNA
<213> ORGANISM: Artificial sequence
<220> FEATURE:
<223> OTHER INFORMATION: Primer targeting GAGE 1-8; sense primer type

<400> SEQUENCE: 7
agttggcgag gaagatcgac                                                20

<210> SEQ ID NO 8
<211> LENGTH: 22
<212> TYPE: DNA
<213> ORGANISM: Artificial sequence
<220> FEATURE:
<223> OTHER INFORMATION: Primer targeting GAGE 1-8; antisense primer
      type

<400> SEQUENCE: 8

-continued

```
cttctttaa cactgtgatt gc                                              22

<210> SEQ ID NO 9
<211> LENGTH: 19
<212> TYPE: DNA
<213> ORGANISM: Artificial sequence
<220> FEATURE:
<223> OTHER INFORMATION: Primer targeting GAGE 1-8; sense primer type
<220> FEATURE:
<221> NAME/KEY: misc_feature
<222> LOCATION: (12)..(12)
<223> OTHER INFORMATION: r = a or g

<400> SEQUENCE: 9
agcctcctga artgattgg                                                 19

<210> SEQ ID NO 10
<211> LENGTH: 21
<212> TYPE: DNA
<213> ORGANISM: Artificial sequence
<220> FEATURE:
<223> OTHER INFORMATION: Primer targeting GAGE 1-8; antisense primer
      type

<400> SEQUENCE: 10
gcgttttcac ctcctctgga t                                              21
```

SELECTED PRIMERS FOR DETECTION OF MAGE OR GAGE GENES FOR DIAGNOSIS OF CANCER AND METHODS OF USE

RELATED INFORMATION

This application is a continuation-in-part of U.S. application Ser. No. 10/258,828, filed Oct. 25, 2002, which was the National Stage of International Application No. PCT/KR01/00681, filed Apr. 24, 2001, which claims priority to Korean Application No. 2000-21837, filed Apr. 25, 2000. The priority of these applications are expressly claimed, and the disclosure is hereby incorporated by reference in their entirety.

BACKGROUND OF THE INVENTION

1. Field of the Invention

The present invention is related to primers for diagnosis of one or more kinds of cancers expressing the MAGE or GAGE genes or their subtypes, and a diagnostic kit containing the above primers. In a particular embodiment, the invention relates to common primers that can simultaneously detect six MAGE sub-types from MAGE 1 to MAGE 6 (MAGE 1–6) or eight GAGE sub-types from GAGE 1 to GAGE 8 (GAGE 1–8), a diagnostic kit containing the above common primers, and methods for use of these primers to detect cancer. Additionally, the invention includes methods for use of primers for detection of MAGE or GAGE expression in a clinical methodology to detect the expression of multiple MAGE and GAGE genes in biological samples, including patient samples for screening, diagnosis, or prognosis in cancer patients. The methodology may also include qualitative correlation of expression of the MAGE or GAGE genes to disease or quantitative measurement of expression of one or more genes to standard or control values, and the use of this comparison in the methodologies listed above.

2. Description of the Prior Art

The diagnosis of cancers has been accomplished through the medical physical examination, X-ray and CT, histological examination, etc. However, these methods have not been appropriate for detection of cancers at the initial stage, for discrimination between a malignant cancer and a benign tumor. It is believed that the initial stages of cancer development cannot be detected by direct physical observation, but occur at the genetic level where a number of genes that are involved in the onset or progression of the cancer are differentially expressed in the very earliest stages of the disease. In some cases, the initial stages of cancer may be marked by the expression of specific genes that either accompany the onset of the disease, or that are the actual causative agent in the onset or progression of cancer. Unfortunately, the ability to detect these events is complicated by the fact that hundreds or thousands of genes may be expressed during the onset of the disease and it is extremely difficult to detect and to separate normal gene expression from the expression of the specific genes that indicate or are responsible for, the onset or progression of disease.

However, recently developed molecular biological diagnostic methods have contributed greatly to the development of cancer diagnostics that are both specific and highly sensitive. The most widely used method among many molecular biological diagnostic methods is the polymerase chain reaction (PCR) or the reverse transcriptase-polymerase chain reaction (RT-PCR). In these techniques, abnormal genes, such as cancerous antigen genes expressed in a sample, are amplified and detected.

Particularly, RT-PCR is a method of detecting mRNA which is expressed by a particular gene. This method may be used for the diagnosis of a cancer by examining the property of expression of cancerous antigen genes. The most important matter in the diagnosis of a cancer in the RT-PCR method is the selection of the target gene for detection (hereinafter referred to as a "cancer diagnosis marker"). Usually, only one cancer diagnosis marker is selected and detected by this method.

The requirements for a cancer diagnosis marker are that it should be selectively expressed in cancerous tissue and should be expressed in large amounts in as many cancer types as possible. MAGE (melanoma antigen gene) and GAGE ('G' antigen gene) are two kinds of cancer-associated testis antigens. Selected subtypes or subfamilies of these genes are expressed in many kinds of cancer tissues, but are not expressed in most normal tissues, except for the testis. It has been clarified that MAGE has been expressed in many cancers such as the stomach cancer (1, 2), esophagus cancer (3), colon cancer (4), lung cancer (5), breast cancer (6, 7), liver cancer (8), leukemia (9), neuroblastoma (10), ovary cancer (11), etc. in many studies since it was discovered in the melanoma. And it has been reported that GAGE has been expressed in the melanoma, sarcoma, small-cell carcinoma, head and neck cancer, bladder cancer, ovary cancer, etc. (11, 12). MAGE or GAGE genes may be identified with distinct nomenclature as subtypes or subfamilies, such as MAGE A–L, and specifically such as MAGE A1–A15, MAGE B1–17, MAGE C1–7, MAGE D1–4, MAGE E1–3, MAGE F, MAGE G, MAGE H, MAGE 11–12, MAGE J1, MAGE K1, MAGE L2 and NECDIN.

Therefore, selected MAGE and GAGE genes are very extensively utilized as cancer diagnostic markers because detection of MAGE and/or GAGE expression detects many kinds of cancers and has a high specificity for expression in cancer tissues compared to other cancer-associated antigens such as the carcinoembryonic antigen, etc. Also, MAGE and GAGE have a high homogeneity of gene sequence among gene subtypes. About 12 kinds of sub-types of MAGE have the homogeneity ranging from about 56% to 99%, and 8 kinds of sub-types of GAGE have the homogeneity ranging from about 82% to 99%. Therefore, it is possible to increase the cancer diagnosis rate by using such same DNA sequence part as a primer since many sub-types of MAGE or GAGE may be detected simultaneously during RT-PCR. De Plaen et al., "Structure, chromosomal localization, and expression of 12 genes of the MAGE family, Immunogenetics 1994;405 (5):360–9; Chomez, Patrick et al., "An Overview of the MAGE Gene Family with the Identification of all Human Members of the Family," Cancer Research 61, 5544–5551, Jul. 15, 2001; Barker, P A, et al., "The MAGE proteins: emerging roles in cell cycle progression, apoptosis, and neurogenetic disease," J. Neurosci Res 2002 March 15:67 (6):705–12; Van den Eynde, B., et al., "A new family of genes coding for an antigen recognized by autologous cytolytic T lymphocytes on a human melanoma," J. Exp. Med. 1995 September 1,;182(3):689–98; and De Backer, Olivier, "Characterization of the GAGE Genes That Are Expressed in Various Human Cancers and in Normal Testis," Cancer Research 59, 3157–3165, Jul. 1, 1999).

Accordingly, the highly conserved, high homogeneity of sequences among MAGE and GAGE subtypes allows the design of common primers of the invention having a high selectivity and specificity for cancer detection and diagnosis. Moreover, the primers of the invention exhibit high specificity for cancer detection and diagnosis through simultaneous detection of many MAGE or GAGE gene subtypes.

SUMMARY OF THE INVENTION

The present invention provides primers for the diagnosis of cancers and a diagnostic kit containing such primers for simultaneous amplification of many sub-types of MAGEs or GAGEs and detection of these genes in RT-PCR. The use of these primers yields reliable markers for rapid and economic screening of biological samples, including samples from human patients, for early detection of cancers characterized by the expression of the MAGE or GAGE genes and their subtypes. The methods disclosed herein can also be used to establish a screening methodology for early-onset cancer detection, a technique for prognosis of disease progression, and/or a program to monitor a patient's response during treatment for MAGE/GAGE expressing cancer types. All of these methodologies enhance the ability of clinicians and scientific researchers to detect, understand, and treat these diseases.

The common primers are derived from comparing the gene sequences of many sub-types in order to detect many sub-types of MAGE and GAGE through an amplification reaction. The primer sequences are obtained from the sequence listings of 12 MAGE genes and 8 GAGE genes registered in GenBank, comparing the DNA sequence of each gene, analyzing the DNA homogeneity of both the MAGE and GAGE genes and subtypes, and selecting a portion or sequence having a high homogeneity. The common primers thus determined are shown in Table 1 as follows:

TABLE 1

| Primer | Cancer diagnostic marker | Type | Sequence |
|---|---|---|---|
| SEQ ID NO.1 | MAGES 1–6 | S | 5'-GGTCACAAAGGCAGAAATGCT-3' |
| SEQ ID NO.2 | MAGES 1–6 | AS | 5'-GCCCTTGGACCCCACAGGAACTC-3' |
| SEQ ID NO.3 | MAGES 1–6 | S | 5'-CTGAAGGAGAAGATCTGCC-3' |
| SEQ ID NO.4 | MAGES 1–6 | AS | 5'-CTCCAGGTAGTTTTCCTGCAC-3' |
| SEQ ID NO.5 | MAGES 1–6 | S | 5'-CTGAAGGAGAAGATCTGCCWGTG-3' |
| SEQ ID NO.6 | MAGES 1–6 | AS | 5'-CCAGCATTTCTGCCTTTGTGA-3' |
| SEQ ID NO.7 | GAGES 1–8 | S | 5'-AGTTGGCGAGGAAGATCGAC-3' |
| SEQ ID NO.8 | GAGES 1–8 | AS | 5'-CTTCTTTTAACACTGTGATTGC-3' |
| SEQ ID NO.9 | GAGES 1–8 | S | 5'-AGCCTCCTGAARTGATTGG-3' |
| SEQ ID NO.10 | GAGES 1–8 | AS | 5'-GCGTTTTCACCTCCTCTGGAT-3' |

In Table 1, S means a sense primer (5' to 3'), AS means an anti-sense primer (3' to 5'), W means A or T, and R means A or G.

SEQ ID NO.1/2 is the primer for MAGE, but shows a false positive reaction in PCR. It is suspected that the reason for a false positive reaction is that it is very likely that the genes are amplified from the contaminated genomic DNA since these primers are located in one exon.

SEQ ID NO.3/4 and SEQ ID NO.5/6 are the primers for MAGE. SEQ ID NO.3 and SEQ ID NO.5 are the primers that are located at the boundary of two exons. No false positive reaction is shown on PCR and nested PCR using SEQ ID NO.3/4 and SEQ ID NO.5/6 since SEQ ID NO.3 and SEQ ID NO.5 does not bind to the genomic DNA.

SEQ ID NO.7/8 and SEQ ID NO.9/10 are the primers for GAGE. SEQ ID NO.7 and SEQ ID NO.8 or SEQ ID NO.9 and SEQ ID NO.10 are located at difference exons, and no false positive reaction is shown in the experiments in which SEQ ID NO.7/8 and SEQ ID NO.9/10 are used since a long intron is inserted between these exons.

The cell lines used for the diagnosis of cancers include the human stomach cancer cell line (SNU484, SNU638, SNU668), head and neck cancer cell line (AMC-HN-3, AMC-HN-4, AMC-HN-7), cervix cancer cell line (HeLa, Caski), lung cancer cell line (NCI H1703, NCI H522), colon cancer cell line (HT29), metastatic prostate gland cancer cell line (LN.CAP), promyelocytic leukemia (HL60) and osteosarcoma cell line (SaOS2). And for the human body cancer tissues and cells, 12 cases of breast cancer, 27 cases of head and neck cancer, 5 cases of stomach cancer, 3 cases of thyroid gland cancer, 3 cases of lymphoma, 1 case of cystic adenoma, 1 case of sarcoma, 1 case of dermatofibrosarcoma, 1 case of malignant mixed tumor, 9 cases of urine cells of the patients of bladder cancer, and 15 cases of abdominal cavity cells of the patients of stomach cancer are used. For the reference benign tumor tissues and cells, 18 cases of benign head and neck tumor, 10 cases of normal white blood cells, and 10 case of urine cells of normal people and of patients of urologic inflammation are used.

Various cancer tissues are kept at -70° C. until they are used, and are pulverized with a grinder after adding RNAzol B (Tel-Test Inc., U.S.A.) to the tissues. The cultured cancer cell lines are dissolved by adding RNAzol B after completely removing the culture medium and washing with the phosphate buffered saline (PBS) solution. The abdominal cavity cells of stomach cancer are collected after opening the abdominal cavity and are mixed with RNAzol B. The normal white blood cells are dissolved completely by adding RNAzol B after only nucleated cells are collected from the blood. The urine cells are mixed with RNAzol B after the cells are collected from the urine.

Separation of RNA from the RNAzol B solution in which various tissues and cells are dissolved is done according to the manufacturer's instructions (Tel-Test., U.S.A.).

The sputum is used for RT-PCR after it is liquefied by adding the equivalent amount of a stabilizer (Roche Diagnostics, Mahnheim, Germany) and mixing thoroughly, and mRNA is separated by using the mRNA separation reagent (Roche Diagnostics, Mahnheim, Germany).

PCR may be used for the diagnosis of cancers by using the common primers of the present company. cDNA is produced by the reverse transcriptase (RT) reaction after extracting the total RNA or mRNA from various cancer tissues, sputum, blood, urine, abdominal cavity cells, etc. of the patients. MAGE 1–6 or GAGE 1–8 are amplified by performing PCR using the common primers of the present invention (SEQ ID NO.1 and 2 or SEQ ID NO.3 and 4 or SEQ ID NO.7 and 8) for cDNA. Many kinds of cancers may be diagnosed simultaneously through detection of MAGE 1–6 or GAGE 1–8 DNA bands by electrophoresis of the product of PCR after performing the secondary PCR (nested PCR) using the common primers of the present invention (SEQ ID NO.5 and 6 or SEQ ID NO.9 and 10) for the primary product of RT-PCR.

In the present invention, RT-PCR is used as a method of amplification of MAGE 1–6 or GAGE 1–8. However, it is not limited to the applications described in the present specification, and various methods of amplification, including those identified specifically below of MAGE 1–8 by using the common primers of the present invention are included and the various parameters in the amplification reaction, e.g. reagents, cycles, etc. are readily determined by one of ordinary skill in the art.

A cancer diagnostic kit including the common primers of the present invention and PCR or RT-PCR reagents may be provided within the present invention. The kit may include reagents for separation of RNA, such as RNAzol, and a stabilizer, reagents for the reverse transcriptase reaction, such as RT buffer, dNTP, MMLV reverse transcriptase, RNase inhibitor, and oligo dT primer and reagents for a first and second PCR amplification reaction, such as PCR buffer, dNTP, sense and antisense primers (as disclosed above,) and Taq polymerase.

BRIEF DESCRIPTION OF THE DRAWINGS

The foregoing and other objects, aspects and advantages will be better understood from the following detailed description of a preferred embodiment of the invention with reference to the drawings, in which:

FIG. 1 shows the affects of processing of MAGE primers and DNase on the detection of MAGE using PCR or RT-PCR where A is the result of PCR of the total RNA using SEQ. ID NO.1/2 and B is the result of PCR by using SEQ ID NO.1/2 after processing DNase to total RNA. C is PCR of total RNA using SEQ ID NO.3/4 and D is PCR of total RNA using SEQ ID NO.3/4 and nested PCR using SEQ ID NO.5/6.

FIG. 2 shows the results of the specificity of detection of MAGE using the RT-PCR method of SEQ ID NO.3/4 and SEQ ID NO.5/6 primers to detect the stomach cancer cell line SNU 484 wherein panel A shows detection of MAGE 1–6 and panel B shows the absence of detection of MAGE 1–6 in normal white blood cells.

FIG. 3 shows the results of measuring each sub-type of MAGE and MAGE 1–6 by using SEQ ID NO.3/4 and SEQ ID NO.5/6 primers in 14 types of cancer cell lines.

FIG. 4 shows the results of measuring each sub-type of MAGE and MAGE 1–6 by using SEQ ID NO.3/4 and SEQ ID NO.5/6 primers in the cancer tissues of the patients of breast cancer.

FIG. 5 shows the results of measuring MAGE 1–6 by using SEQ ID NO.3/4 and SEQ ID NO.5/6 primers in the head and neck cancer (A) and benign head and neck tumor (B).

FIG. 6 shows the results of measuring each sub-type of MAGE and MAGE 1–6 by using SEQ ID NO.3/4 (left panel) and SEQ ID NO.5/6 (right panel) primers in the cancer tissues of the patients of head and neck cancer.

FIG. 7 shows the results of measuring MAGE 1–6 by using SEQ ID NO.3/4 and SEQ ID NO.5/6 primers in other cancer tissues, thyroid gland cancer (A), lymphoma (B), cystic adenoma (C), sarcoma (D), dermatofibrosarcoma (E), malignant mixed tumor (F), abdominal cavity cell of the patients of stomach cancer (G), urine of the patients of bladder cancer (H), and urine cells (I).

FIG. 8 shows the results of measuring GAGE 1–8 by using SEQ ID NO.7/8 and SEQ ID NO.9/10 primers in 14 cancer cell lines.

FIG. 9 shows the results of measuring GAGE 1–8 by using SEQ ID NO.7/8 and SEQ ID NO.9/10 primers in the cancer tissues and urine cells.

FIG. 10 shows the results of measuring MAGE 1–6 by using SEQ ID NO.3/4 and SEQ ID NO.5/6 primers in the lung cancer tissues and sputum.

FIG. 11 shows the results of measuring MAGE 1–6 by using SEQ ID NO.3/4 and SEQ ID NO.5/6 primers in the blood.

DETAILED DESCRIPTION OF PREFERRED EMBODIMENTS OF THE INVENTION

The present invention is illustrated in more detail in the specific examples below, although the content of the present invention is not limited to the specific embodiments disclosed, but rather to the claimed subject matter and the full range of equivalents.

"Amplification" refers to any means by which a polynucleotide sequence is copied and thus expanded into a larger number of polynucleotide molecules, e.g., by reverse transcription, polymerase chain reaction, ligase chain reaction, sequence replication, or replicase amplification, among others.

"Diagnosis" refers to the presence of, or a value determined for, an analyte in a subject sample, which then may be compared to the absence of, or a normal range of the analyte in a sample (e.g., from a healthy individual) such that the relative comparison of the values provides a reference for diagnosing a designated disease. Depending upon the method of detection, the diagnostic value may be a determination of the analyte, but it is not necessarily a quantitated amount. The diagnostic value may also be a relative value, such as a plus or a minus score, and also includes a single value indicating the presence or absence of the analyte in a sample.

"Primer" refers to a polynucleotide that is capable of specifically hybridizing to a designated polynucleotide template and providing a point of initiation for synthesis of a complementary polynucleotide. Such sysnthesis occurs when the polynucleotide primer is placed under conditions in which synthesis is induced, i.e., in the presence of nucleotides, a complementary polynucleotide template, and an gent for polymerization such as DNA polymerase.

"Prognosis" refers to the use of the presence of, or concentration of, an analyte in a subject biological sample that is consistent with a particular expected outcome for a designated disease. The presence or amount (including a zero amount) of the analyte detected in a sample is correlated with a value that indicates the likely outcome of the progression of the disease.

Firstly, the gene expression of MAGE and GAGE and the manufacture of primers are illustrated. The DNA sequences are compared and analyzed by using the DNAsis program after obtaining the information on 12 kinds of MAGE genes and 8 kinds of GAGE genes registered in GenBank. It is shown that the homogeneity of genes of the MAGE type (cDNA) is 56%–99% and the homogeneity of genes of the GAGE type (cDNA) is 82%–99%. The portions having the same or similar DNA sequence of each sub-type are designed to be the primers.

The synthesis is completed after mounting dATP, dTTP, dCTP, and dGTP which are the materials for primer synthesis and the columns for synthesis to the automatic DNA synthesizer (Expedite™ Nucleic Acid Synthesis System of PerSeptive Biosystem Company) and inputting the sequence to be synthesized. The synthesized primers are used by measuring their concentrations with a UV spectrophotometer after the ammonia processing procedure and refining procedure. The primers thus manufactured are shown in Table 1. The primers disclosed herein may differ slightly in sequence and length while maintaining the function of serving as an initiation point for synthesis of a target polynucleotide, as in RT-PCR and PCR reactions. As noted above, the use of RT-PCR or ordinary PCR reactions as an amplification method is merely one example of the use of the primers of the invention. Thus, although PCR and RT-PCR are described in the following examples, amplification by other in vitro methods, such as the ligase chain reaction (LCR), the transcription-based amplification system (TAS), the self-sustained sequence replication system (3SR) and the Qβ replicase amplification.

Presumably, SEQ ID NO.1 and SEQ ID NO.2 (SEQ ID NO.1/2) and SEQ ID NO.3 and SEQ ID NO.4 (SEQ ID NO.3/4) are the MAGE primers and are used for RT-PCR or the primary PCR, and SEQ ID NO.5 and SEQ ID NO.6 (SEQ ID NO.5/6) are used for the secondary PCR (nested PCR).

SEQ ID NO. and SEQ ID NO.8 (SEQ ID NO.7/8) and SEQ ID NO.9 and SEQ ID NO.10 (SEQ ID NO. 9/10) are the primers for the detection of GAGEs, where SEQ ID NO.7/8 is used for RT-PCR or the primary PCR, and SEQ ID NO.9/10 is used for the nested PCR.

Secondly, the procedures for separation of the total RNA are described below:

Various cancer tissues are kept at −70° C. before they are used. The tissues are pulverized with a grinder after adding 1–2 ml of RNAzol B (Tel-Test Inc., U.S.A.) to the tissues. The cultivated cancer cell lines are separated by adding RNAzol B after completely removing the culture medium and washing culture plate once with the PBS. The abdominal cavity cells of stomach cancer are collected through centrifugal separation at 1,200 rpm for 5 minutes after collecting the abdominal cavity cells by adding 100 ml of physiological saline solution to the lower abdominal cavity after opening the abdominal cavity. After the cells are washed once with the PBS, they are mixed by adding RNAzol B to the cell pellet. In the separation of normal white blood cells, only nucleated cells are collected through centrifugal separation at 1,200 rpm for 5 minutes after letting them stand still for 17 seconds after adding 20 ml of sterilized distilled water (DEPC-DW) to 5 ml of the blood containing an anti-coagulant and mixing by adding 20 ml of the twice-concentrated PBS. The cells are dissolved completely by adding 1 ml of RNAzol B to the cells collected. The urine cells are collected through centrifugal separation of 150 ml of urine. The cells are washed once by adding the PBS and are mixed with 1 ml of RNAzol B.

The protein layer and RNA are separated from each other through centrifugal separation at 12,000 rpm for 15 minutes after adding the 1/10 portion of chloroform to the RNAzol B solution in which various tissues and cells are dissolved and mixing them thoroughly. And the RNA solution of the separated supernatant is collected carefully and transferred into a 1.5-ml test tube. RNA is precipitated by adding 100% isopropanol in the same amount to the RNA solution, mixing, and keeping at −20° C. for longer than 16 hours. Then RNA is precipitated through centrifugal separation of the mixed RNA-isopropanol solution at 12,000 rpm, the supernatant is removed, RNA precipitates are washed by adding 1 ml of 70% cold ethanol to the above, and the upper ethanol solution is removed completely through centrifugal separation, RNA precipitates are dissolved into the sterilized distilled water (DEPC-DW), and the concentration and purity of RNA are measured by using a spectrophotometer. An aliquot of the prepared RNA is digested with DNase by addition 100 μg of RNA to the DNase solution (20-mM MgCl$_2$, 20-mM tris-HCL, 0,4-U DNase 1, 0.8-U RNasin), at 37 for 1 hour. The RNA is extracted again as described above and is then used for RT-PCR or RNA PCR.

The sputum is completely liquefied by adding a stabilizer (Roche Diagnostics, Mahnheim, Germany) in the same amount and mixing thoroughly, and mRNA is separated by using a separation reagent (Roche Diagnostics, Mahnheim, Germany) and is used for RT-PCR.

Thirdly, the total RNA is collected and PCR is performed as follows in order to see if the sample RNA is contaminated with MAGE genomic DNA. In the first step, the PCR reaction solution is made by mixing 3 μl of the 10×PCR buffer solution, 1.8 μl of 250-mM MgCl$_2$, 0.3 μl of 10-mM dATP, 0.3 μl of 10-mM dGTP, 0.3 μl of 10-mM dTTP, 0.3 μl of 10-mM dCTP, 0.25 μl of 50 μM sense and anti-sense primers, and 0.25 μl of the Taq polymerase (5 U/μl, Promega Co., U.S.A.) to make up 25 μl of the final PCR reaction solution. The PCR reaction solution is put into a PCR tube, 5 μl of the total RNA solution (0.1 μg/μl) is added to the above solution and mixed, 1 drop of a mineral oil is added, and the entire solution is put into a PCR machine (Cetus 480, Perkin Elmer Co., U.S.A.) in order to perform PCR under the following conditions: Firstly, DNA is denatured by heating the above solution at 94° C. for 5 minutes and reacting for 30–35 cycles in which 1 cycle is for 30 seconds at 94° C., 45 seconds at 57° C., and 45 seconds at 72° C. Finally, PCR is completed by treating the above solution at 72° C. for 5 minutes. The amplified DNA bands are observed by using a UV transilluminator after adding the product of PCR to 1% agarose gel and electrophoresis. Basic PCR methods are described in, for example, U.S. Pat. No. 4,683, 195; Mullis et al. (1987) Cold Spring Harbor Symp. Quant. Biol. 51:263; and Erlich, ed., PCR Technology, (Stockton Press, NY, 1989).

Fourthly, the reverse transcriptase-polymerase chain reaction (RT-PCR) is performed. RNA is denatured by keeping the total RNA solution in a 70° C. water bath for 10 minutes and kept in ice. Firstly, 2 μl of the 5×RT buffer solution, 0.25 μl of 10-mM dATP, 0.25 μl of 10-mM dGTP, 0.25 μl of 10-mM dTTP, 0.25 μl of 10-mM dCTP, 0.25 μl of MMLV reverse transcriptase (200 U/μl), 0.25 μl of RNase inhibitor (28 U/μl), 0.5 μl of 50-μM oligo dT primer, and 4 μl of the sterilized distilled water (DEPC-DW) are put into a PCR tube in order to make an RT reaction solution. To the RT reaction solution, 2 μl of the total RNA solution (1 μg/μl) that is kept in ice is added and 1 drop of a mineral oil is added, and the entire solution is kept at a room temperature for 10 minutes. The reverse transcriptase reaction is completed by putting this test tube into the PCR machine and treating with heat at 42° C. for 60 minutes. The product of reverse transcriptase reaction is then diluted with distilled water at the ratio of 1:1 and is used for PCR. PCR is performed under the following conditions by adding 5 μl of the product of reverse transcriptase reaction into 25 μl of the PCR reaction solution as described in the above, mixing them, adding 1 drop of a mineral oil, and putting the solution into the PCR machine: Firstly, DNA is denatured by heating the solution at 94° C. for 5 minutes and reacting for 18–35 cycles in which 1 cycle is for 30 seconds at 94° C., 45 seconds at 57° C., and 45 seconds at 72° C., and PCR is completed by processing the above at 72° C. for 5 minutes finally.

Fifthly, in the nested PCR, the product of a first PCR or RT-PCR amplification reaction is diluted 10 times with distilled water, its 5-μl portion is taken, and a second PCR amplification is performed after adding PCR reagents as described in the above.

Sixthly, the affects of processing of the MAGE primer and DNase on the detection of MAGE are reviewed.

The total RNA is extracted from the cultured stomach cancer cell line (SNU484, SNU638, SNU668), head and neck cancer cell line (AMC-HN-3, AMC-HN-4, AMC-HN-7), cervix cancer cell line (HeLa, Caski), lung cancer cell line (NCI H1703, NCI H522), colon cancer cell line (HT29), metastatic prostate gland cancer cell line (LN.CAP), and promyelocytic leukemia (HL60) and osteosarcoma cell line (SaOS2), after which PCR and RT-PCR for detecting MAGE are performed. (Refer to FIG. 1.)

A in FIG. 1 is the result of PCR of the total RNA by using SEQ ID NO.1/2, and B is the result of PCR of the total RNA by using SEQ ID NO.1/2 after processing DNase to the total RNA. C is the result of PCR of the total RNA by using SEQ ID NO.3/4, and D is the result of PCR of the total RNA by using SEQ ID NO.3/4 and further of nested PCR by using SEQ ID NO.5/6. It is necessary to perform DNase processing in order to use SEQ ID NO.1/2, but MAGE may be detected without DNase processing by SEQ ID NO.3/4 and SEQ ID NO.5/6, and no false positive reaction by the amplification of genomic DNA is shown. SEQ ID NO.3/4 and SEQ ID NO.5/6 may detect at least one of 6 kinds of sub-types of MAGE (MAGE 1–6) from MAGE 1 to MAGE 6.

Seventhly, the cancer diagnosis specificity of the RT-PCR method by using SEQ ID NO.3/4 and SEQ ID NO.5/6 is evaluated. In order to study the specificity of the RT-PCR method by using SEQ ID NO.3/4 and SEQ ID NO.5/6, the SNU484 cell line and normal white blood cells are extracted to perform RT-PCR and nested PCR. The results show that MAGE 1–6 are detected only in RT-PCR and nested PCR in SNU484, and genomic DNA is not amplified when PCR and nested PCR are performed. (Refer to FIG. 2, panel A.) Further, no MAGE 1–6 is detected in normal white blood cells. (Refer to FIG. 2, panel B.)

Eighthly, in the measurement of MAGEs in the cancer cell line, each sub-type of MAGE and MAGE 1–6 are measured for 14 kinds of cancer cell lines. Each sub-type of MAGE is detected by RT-PCR using SEQ ID NO.3 and MAGE sub-type specific primers. MAGE 1–6 is detected by RT-PCR using SEQ ID NO.3/4 and nested PCR using SEQ ID NO.5/6. The experiments for measuring MAGE 1–6 show a higher positive rate (78.6%) compared to that in the measurement of each sub-type. (Refer to FIG. 3.)

Ninthly, in the measurement of MAGEs in the breast cancer, each sub-type of MAGE and MAGE 1–6 are measured for the cancer tissues of the patients of breast cancer. RT-PCR having SEQ ID NO.3/4 as a primer and nested PCR using the SEQ ID NO.5 primer and MAGE sub-type specific primer are performed, but RT-PCR using SEQ ID NO.3/4 and nested PCR using SEQ ID NO.5/6 are performed for the detection of MAGE 1–6. A higher positive rate (91.2%) is shown in the measurement of MAGE 1–6 compared to that in the measurement of each sub-type. (Refer to FIG. 4.)

Tenthly, in the measurement of MAGEs in the head and neck cancer and benign head and neck tumor, MAGE 1–6 are measured. MAGE 1–6 is measured by RT-PCR using SEQ ID NO.3/4 and nested PCR using SEQ ID NO.5/6. Among 27 cases of cancers, 19 cases are positive (70.3%), and none is detected in the benign tumor. (Refer to FIG. 5, where M means a size marker and – is PCR without adding cDNA.)

Eleventhly, in the measurement of MAGE sub-types in the head and neck cancers, each sub-type of MAGE and MAGE 1–6 are measured in the samples in which MAGE 1–6 are detected among the samples of head and neck cancer. RT-PCR using SEQ ID NO.3/4 as a primer and nested PCR using the SEQ ID NO.5 and MAGE sub-type specific primers are performed, and MAGE 1–6 are measured in terms of RT-PCR and nested PCR by using SEQ ID NO.3/4 and SEQ ID NO.5/6, respectively. The method of measurement of each sub-type has a lower efficiency than that of the method of detection of MAGE 1–6. (Refer to FIG. 6.)

Twelfthly, the measurement of MAGE 1–6 in other cancer tissues and abdominal cavity and urine cells is reviewed.

MAGE 1–6 are measured in terms of RT-PCR and nested PCR by using SEQ ID NO.3/4 and SEQ ID NO.5/6, respectively. The objects of measurement include the thyroid gland cancer (A), lymphoma (B), cystic adenoma (C), sarcoma (D), dermatofibrosarcoma (E), malignant mixed tumor (F), abdominal cavity cell of the patients of stomach cancer (G), urine of the patients of bladder cancer (H), and urine of the patients of other diseases (I). (Refer to FIG. 7, where M means a size marker, and – is PCR without adding cDNA.)

No MAGE 1–6 are detected in the thyroid gland cancer, but various kinds of MAGEs are detected in the abdominal cells of the patients of remaining cancers and stomach cancer and the urine cells of the patients of bladder cancer.

Thirteenthly, in the measurement of GAGEs in cancer tissues and urine cells, GAGE 1–8 of 14 kinds of cancer cell lines are measured. GAGE 1–8 are measured in terms of RT-PCR or PCR using SEQ ID NO.7/8 or nested PCR using SEQ ID NO.9/10.

No GAGE is detected in case of PCR and nested PCR without the reverse transcriptase reaction, and positive reactions are shown in 13 reactions among 14 reactions (92.9%) in case of PCR and nested PCR after the reverse transcriptase reaction. (Refer to FIG. 8.) In the stomach cancer, 80% of reactions are shown to be positive to GAGEs, 85.7% is shown to be positive in the breast cancer, and 55.6% is shown to be positive in the urine cells of bladder cancer. And no positive reactions are shown in the urine of the patients of diseases other than the cancer. (Refer to FIG. 9.)

Fourteenthly, in the measurement of MAGEs in the lung cancer tissues and sputum, MAGE 1–6 are measured in 8 cases of lung cancer tissues, 14 cases of sputum of the patients of lung cancer, and 16 cases of sputum of hospitalized patients of diseases other than the lung cancer. They are measured in terms of RT-PCR and nested PCR by using SEQ ID NO.3/4 and SEQ ID NO.5/6, respectively. MAGE 1–6 are detected in 7 cases among 8 cases of lung cancer tissues, and 4 cases among 14 cases of sputum of the patients of lung cancer. And no MAGEs are detected at all in 16 cases of sputum of hospitalized patients of diseases other than the lung cancer. (Refer to FIG. 10.)

Fifteenthly, in the measurement of MAGEs in the blood, MAGEs are measured in 20 cases of the blood of patients of cancer and 15 cases of the blood of normal people. They are measured in terms of RT-PCR and nested PCR by using SEQ ID NO.3/4 and SEQ ID NO.5/6, respectively. MAGE 1–6 are detected in 3 cases among 20 cases of the blood of the patients of cancer, and none is detected in the blood of normal people. (Refer to FIG. 11, where + is a sample in which 5 cells of SNU484 (MAGEs 1–6 benign cells) to 5 ml of the blood of normal people.)

Primer SEQ ID NO.3/4 and SEQ ID NO.5/6 that detect MAGE 1 to MAGE 6 simultaneously and SEQ ID NO.7/8 and SEQ ID NO.9/10 that detect GAGE 1 to GAGE 8 simultaneously may be used as cancer diagnostic kits having a high specificity and a high diagnosis rate of cancer compared to the method of measuring each sub-type.

The primers of the invention have a very high specificity for the diagnosis of cancers, none is shown to be positive in various normal cells or benign tumors, and they can detect MAGEs in urine cells or sputum cells. The primers may be used for cancer diagnostic kits for non-hygroscopic samples, as well as tissues. The present invention is also advantageous in that the time and expenses may be reduced through simultaneous measuring of many sub-types of MAGEs or GAGEs.

In addition to the foregoing description of the design and synthesis of the primers (SEQ ID NO. 1–10), the invention also includes a method for detecting, a method for obtaining a diagnosis of a method for determining the prognosis of, or a method of monitoring the progression of cancers, including breast, head and neck, stomach, dermal, thyroid, lymphoma, cystic, sarcoma, prostate, dermatological, cervix, bladder, lung, colon, and stomach, including others. In each cancer type, the common element for detection pursuant to this invention is expression of the MAGE or GAGE family or subfamily of genes identified by the primers disclosed herein. It should be noted that the first members of the human MAGE family were identified as genes encoding a tumor specific antigen. This gene was later found to belong to a cluster of genes located on the X chromosome. Subsequent studies involving subfamilies of the major MAGE gene clusters have determined that certain subfamilies are completely silent in normal tissues, with the exception noted above, of male germ cells, and some are expressed in tumor cells of various histological types where they code for antigens recognized by cytolytic delymphosites. The specific expression in tumor cells makes the antigens of particular utility for detection in cancer cells when expressed by a gene of the underlying family. However, the detection of expression profiles of various MAGE or GAGE subtypes in varying tissues may show both cancer-specific or ubiquitous expression. Thus, while the research and characterization of MAGE and GAGE genes and their subtypes is expected to continue, the foundation of the present invention rests on the ability to use the primers disclosed herein to detect selected groups of members of the MAGE or GAGE gene families that are differentially expressed in cancer, as compared to normal or benign tissue.

The methodology of the present invention is performed by extracting RNA from a biological sample, such as a sample of tissue or body fluid taken from a patient. The basic method of diagnosis includes:

1) The separation of total RNA from cancer tissue or cancer cells,

2) The synthesis of cDNA by reverse transcription (RT) reaction using RT buffer, dNTP, MMLV reverse transcriptase, RNase inhibitor oligo dT primer, 3) The amplification of cDNA of MAGE or GAGE by polymerase chain reaction (PCR) using PCR buffer, dNTP, sense and antisense primers, Taq polymerase and RT reaction products (cDNA), 4) The amplification of cDNA of MAGE or GAGE by $2^{nd}$ (nested) PCR using PCR buffer, dNTP, sense and antisense primers, Taq polymerase, 5) The identification of amplified cDNA ($2^{nd}$ PCR products) of MAGE or GAGE by electrophoresis, and the correlation of the identification of MAGE or GAGE expression to a diagnosis, prognosis, or monitoring of the onset or progression of disease.

The correlation step may be taken as a relative expression level of the underlying gene, or simply a positive or negative indication of whether or not gene expression is present in the underlying sample.

In one embodiment of the invention, the expression of the members MAGE or GAGE gene family in the biological sample from a cancer patient is monitored over time for diagnosis or assessment of the prognosis for cancer in the subject patient. In this embodiment, the expression of the MAGE or GAGE gene families are measured at one or more time to monitor the same parameters over a succession of time intervals in patients having cancer. The expression of the gene may also be compared over time to determine the progress of the disease and/or the prognosis of the patient when the analyses are made in combination with therapeutic intervention. Generally, an increase in the gene expression of the MAGE or GAGE gene families, or an increase in the number of subtypes indicates the continuing presence of the disease.

In one embodiment of the invention, the measurement of the expression of MAGE or GAGE genes or their subfamilies is combined with the measurement of other tumor markers such as CA125, soluble IL.2 receptor, tumor necrosis factor (TNF), CSF, CEA, PSA, CA 19.9, BRCA 1, differential lipid analysis, including lysophospholipid profiling, proteomics screening, or tissue biopsy. In this embodiment, the measurement of the MAGE and GAGE gene family expression is used in combination with other determinations for the detection, prognosis, diagnosis, or other methodologies described above. The use of these other methodologies in combination with the expression of MAGE or GAGE cancer types improves the sensitivity and/or specificity of an overall cancer detection method. In each of these approaches, the presence of a particular marker is preferably compared to a normal or controlled value. In the case of the expression of the MAGE or GAGE genes, the normal or controlled values may be a complete absence of the expression of the genes in the tissue or body fluid sample. Alternatively, the normal or control value may be the expression at a lower level or the measurement of expression after subtraction of a background value that may represent the contamination of a sample with genomic DNA.

The cancer detection, prognosis, and monitoring functions of the present invention can be combined with a general assessment of the success of one particular type of anti-cancer therapy and can be used as part of a monitoring procedure during the continued analysis of the progression of disease in a particular cancer patient. Thus, the methodology of the present invention includes measurement of the expression of MAGE and GAGE genes in a cancer patient who is receiving anti-cancer therapy, as a measurement of the progress of the therapy and the relative presence or absence of the cancer over time.

The use of the MAGE and GAGE gene expression diagnostic capability may reduce or eliminate the need for repeated biopsies and can distinguish between a benign and malignant growth. Furthermore, where a particular cancer has apparently entered a state of remission, the continued use of a diagnostic methodology pursuant to this invention may allow for the early detection of a recurrence, i.e., through detecting the re-initiation or onset of MAGE or GAGE gene expression and can thereby provide a valuable monitoring procedure in a significant patient population.

Because the MAGE or GAGE gene expression assists in distinguishing between a benign and malignant tumor, the diagnostic embodiment of the invention may help distinguish whether a tumor or growth constitutes a condition that requires surgical intervention or whether an alternative treatment is suggested.

As described above, each of the methodologies of the invention may include the specific step of determining MAGE or GAGE family subtype expression. The methodology of the invention includes measuring between 1 and 6 MAGE gene types and between 1 and 8 GAGE gene types. A particular patient may be repeatedly monitored for expression of different MAGE or GAGE subtypes and the initial detection, or detection over time, of different MAGE or GAGE family subtypes may provide a profile that yields significant information about the underlying disease state or disease progression such that different monitoring or intervention is justified. Where such profiling enables the researcher or clinician to distinguish between cancer types, the use of MAGE or GAGE gene family expression can distinguish the origin of a malignant tumor in a patient that may be exhibiting multiple tumor types.

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims. All references cited herein are specifically incorporated in their entirety.

REFERENCES

1) Li J, Yang Y, Fujie T, Tanaka F, Mimori K, Haraguchi M, Ueo H, Mori M, and Akiyoshi T, "Expression of the MAGE gene family in human gastric carcinoma," Anticancer Res. 17:3559–3563, 1997.
2) Inoue H. Li J, and Honda M, "MAGE-1 mRNA expression in gastric carcinoma," Gastroenterol 109: 1522–1525, 1995.
3) Inoue H, Mori M, and Honda M, "Human esophageal carcinomas frequently expressing the tumor-rejection antigens of MAGE genes," Int J Cancer 63: 523–526, 1995.
4) Mori M, Inoue H, and Mimori K, "Expression of MAGE genes in human colorectal carcinoma," Ann Surg 224: 183–188, 1996.
5) Weynants P, Lethe B, Brasseur F, Marchand M, and Boon T, "Expression of MAGE genes by non-small cell lung carcinomas," Int J Cancer 56: 826–829, 1994.
6) Russo M, Traversari C, and Verrecchia A, "Expression of MAGE gene family in primary and metastatic human breast cancer: Implications for tumor-specific immunotherapy," Int J Cancer 64: 216–221, 1995.
7) Fujie T, Mori M, Ueo H, Sugimachi K, and Akiyoshi T, "Expression of MAGE and BAGE genes in Japanese breast cancers," Ann Oncol 8: 369–372, 1997.
8) Yamashita N, Ishibashi H, Hayashida K, Kudo J, Takenaka K, Itoh K, and Niho Y, "High frequency of the MAGE-1 gene expression in hepatocellular carcinoma," Hepatology 24: 1437–1440, 1996.
9) Shichijo S, Tsunosue R, Masuoka K, Natori H, Tamai M, Miyajima J, Sagawa K, and Itoh K, "Expression of the MAGE gene family in human lymphocytic leukemia," Cancer Immunol Immunother 41: 90–103, 1995.
10) Corrias M V, Scaruffi P, Occhino M, De Bernardi B, Tonini G P, and Pistoia V, "Expression of MAGE-1, MAGE-3 and MART-1 genes in neuroblastoma," Int J Cancer 69: 403–407, 1995.
11) Russo V, Dalerba P, Ricci A, Bonazzi C, Leone B E, Mangioni C, Allavena P, Bordignon C, and Traversari C, "MAGE, BAGE and GAGE genes expression in fresh epithelial ovarian carcinomas," Int J Cancer 67: 457–460, 1996.
12) Van den Eynde B, Peeters O, De Backer B, Gaugler S, Lucas, and Boon T, "A new family of genes coding for an antigen recognized by autologous cytolytic T lymphocytes on a human melanoma," J Exp Med 182: 689, 1995.

What is claimed is:

1. A method for detection of cancer by detecting expression of MAGE genes comprising: providing a biological sample, extracting RNA from the sample, detecting MAGE gene expression by an in vitro amplification reaction using a primer pair selected from the group consisting of SEQ ID NOS. 3 and 4, and SEQ ID NOS. 5 and 6.

2. The method of claim 1 wherein the biological sample is a tissue sample selected from the group consisting of breast, head and neck, stomach, thyroid, lymphoid, bladder, dermal, stomach, cyst, lung, cervix, colon, and prostate.

3. The method of claim 1 wherein the biological sample is derived from blood.

4. The method of claim 2 further comprising comparing the detected MAGE gene expression to MAGE gene expression in a control biological sample.

5. The method of claim 1 wherein the amplification reaction is polymerase chain reaction.

6. The method of claim 1 wherein the step of detection of MAGE expression by an amplification reaction is comprised of a first RT-PCR reaction yielding a first amplified product followed by a second PCR reaction.

7. The method of claim 6 wherein the first RT-PCR reaction uses the primer pair of SEQ ID NO. 3 and 4.

8. The method of claim 6 wherein the second PCR reaction uses the primer pair of SEQ ID NO. 5 and 6.

* * * * *

UNITED STATES PATENT AND TRADEMARK OFFICE
CERTIFICATE OF CORRECTION

PATENT NO. : 7,098,008 B2  
APPLICATION NO. : 10/286380  
DATED : August 29, 2006  
INVENTOR(S) : Jong Wook Park and Chang-Ho Jeon It is certified that error appears in the above-identified patent and that said Letters Patent is hereby corrected as shown below:

On the title page of the patent, please change

Item
"(73) Assignee: iC&G DO Ltd."

to

--(73) Assignee: iC&G Co. Ltd. --

Signed and Sealed this

Second Day of January, 2007

JON W. DUDAS  
*Director of the United States Patent and Trademark Office*